United States Patent [19]
Matsui et al.

[11] Patent Number: 5,125,040
[45] Date of Patent: Jun. 23, 1992

[54] INSPECTION METHOD OF PHOTOMASK RETICLE FOR SEMICONDUCTOR DEVICE FABRICATION

[75] Inventors: Shogo Matsui, Sagamihara; Kenichi Kobayashi, Tokyo, both of Japan

[73] Assignee: Fujitsu Ltd., Kawasaki, Japan

[21] Appl. No.: 587,557

[22] Filed: Sep. 24, 1990

Related U.S. Application Data

[63] Continuation of Ser. No. 309,036, Feb. 13, 1989, abandoned, which is a continuation of Ser. No. 139,148, Dec. 24, 1987, abandoned, which is a continuation of Ser. No. 880,092, Jun. 3, 1986, abandoned, which is a continuation of Ser. No. 620,089, Jun. 13, 1984, abandoned.

[30] Foreign Application Priority Data

Jun. 23, 1983 [JP] Japan ............... 58-113230

[51] Int. Cl.$^5$ ............... G06K 9/68
[52] U.S. Cl. ............... 382/34; 382/8; 382/48; 358/101
[58] Field of Search ............... 382/8, 30, 34, 41, 48; 358/101, 106, 107; 356/235, 388, 390, 392

[56] References Cited

U.S. PATENT DOCUMENTS

| | | | |
|---|---|---|---|
| 4,056,716 | 11/1977 | Baxter et al. | 382/8 |
| 4,242,662 | 12/1980 | Tsujiyama et al. | 382/48 |
| 4,441,207 | 4/1984 | Lougheed et al. | 382/41 |
| 4,448,532 | 5/1984 | Joseph et al. | 356/237 |
| 4,477,926 | 10/1984 | Linger et al. | 382/8 |
| 4,491,962 | 1/1985 | Sakou et al. | 382/8 |
| 4,532,650 | 7/1985 | Wihl et al. | 382/8 |
| 4,543,660 | 9/1985 | Maeda | 382/34 |
| 4,555,798 | 11/1985 | Broadbent, Jr. et al. | 382/8 |
| 4,570,180 | 2/1986 | Baier et al. | 358/106 |
| 4,579,455 | 4/1986 | Levy et al. | 358/106 |
| 4,589,139 | 5/1986 | Hada et al. | 382/8 |

FOREIGN PATENT DOCUMENTS 2129547 5/1984 United Kingdom.

OTHER PUBLICATIONS

Review of the Electrical Communications Laboratories, vol. 30, No. 6, 1982, pp. 1076-1085, Tokyo, JP; B. Tsujiyama et al.: "An automated mask defect inspection".

Primary Examiner—David K. Moore
Assistant Examiner—Jose L. Couso
Attorney, Agent, or Firm—Staas & Halsey

[57] ABSTRACT

A method of inspecting a photomask reticle for the fabrication of a semiconductor device such as a die having a first pattern which has its own individual shape and a plurality of second patterns each having the same shape and size among themselves, combining the methods of the database inspection and of the pattern comparing inspection. The method of database inspection is applied to the first pattern and to one of the second patterns selected randomly. The database inspection can be performed by comparison with inspection data derived from design data used for the fabrication of the photomask reticle, such as by an improved reticle tester which can exclude all of the second patterns except the selected one of the second patterns. The second patterns other than the selected pattern are then inspected by the method of the pattern comparing inspection, that is, by comparison with the selected second pattern which has already been inspected by the database inspection. The volume of the storage for the inspection data and the time required to inspect the photomask reticle can be reduced to less than one fourth of those in the prior art inspection method, while maintaining high accuracy in the inspection of photomask reticles.

7 Claims, 3 Drawing Sheets

INSPECTION METHOD OF PHOTOMASK RETICLE FOR SEMICONDUCTOR DEVICE FABRICATION

This is a continuation of copending application Ser. No. 07/309,036 filed on Feb. 13, 1989, now abandoned, which is a continuation of Ser. No. 07/139,148, abandoned, which is a continuation of Ser. No. 06/880,092 abandoned, which is a continuation of Ser. No. 06/620,089, abandoned.

BACKGROUND OF THE INVENTION

The present invention relates to a method of inspecting a photomask reticle used in the fabrication of a semiconductor device. More specifically, this invention relates to a method of inspecting a photomask reticle for a large scale integrated circuit (LSI) or a very large scale integrated circuit (VLSI), using inspection data stored in a storage medium such as a magnetic tape. This method is referred to as a database inspection method.

Recently, as a result of the tremendously high packing density of semiconductor devices, the photomask pattern is becoming dazzlingly complex and microscopic. Since the photomask reticle corresponds to a mother pattern for fabricating the semiconductor device, it is most important to keep the reticle in excellent condition. A defect in its pattern, even a very microscopic one, cannot be allowed to exist.

Typically, in a LSI or VLSI semiconductor die, a plurality of semiconductor elements having the same pattern are fabricated. The inspection of the photomask reticle for this purpose was at first performed visually by the human eye using a microscope for comparison with an adjacent identical standard pattern. This visual inspection was then replaced by a "pattern comparing inspection" (also referred to as a "mask comparing inspection"), namely an automated optical comparison inspection using an image sensor such as a charge-coupled device (CCD) camera and an electronic circuit for comparing the image with a standard pattern.

However, recently, the pattern of the die has become so complicated that it becomes difficult to inspect correctly by only the pattern comparing inspection method. Further, as the pattern comparing inspection requires a standard pattern for the comparison, if the standard pattern has a defect, the whole inspection is caused to be a failure. Furthermore, if the die is composed of only a single pattern which does not have portions with the same shape and size, the pattern comparing inspection cannot be applied. On the other hand, a method of designing the reticle pattern by a computer technique, such as a CAD (computer aided design) system, using a "design database" has been developed. Consequently, the concept of the CAD system has been introduced to the inspection process, so that the inspection has come to be made by an "inspection database", which inspection is referred to as a "database inspection".

When the database inspection was first introduced, the design data was used for the database inspection, but lately an "inspection database" is itself provided, because it makes the inspection process easy and avoids any overlapping faults as between both the fabrication and the inspection. By applying the database inspection method, the accuracy of the inspection becomes very high.

The database inspection can be made by an apparatus called a "reticle tester", in which the inspection data for the reticle pattern is stored in a storage medium such as a magnetic tape. However, the volume of the inspection data becomes enormous because of too much complexity and too many kinds of the recent semiconductor devices, so that providing a space to stock the storage media has become almost impossible, and the inspection has come to require a large amount of time. These are becoming big problems for inspection of photomask reticles, but the database inspection method is needed to maintain the very high accuracy.

SUMMARY OF THE INVENTION

Therefore, the object of the present invention is to save on the space required for stocking the inspection data media, and the time to perform the prior art inspection, by applying substantially the database inspection method, while keeping the accuracy of the inspection. The present invention can be performed by combining the method of the database inspection and the pattern (or mask) comparing inspection so that the latter method is applied to the reticle patterns having the same shape and size in the photomask reticle.

By applying the present invention to the inspection of photomask reticles, the high accuracy of the inspection can be maintained by using the database inspection while the space for storage of the database and the time for the inspection can be saved by the use of the pattern comparison method.

BRIEF DESCRIPTION OF THE DRAWINGS

FIGS. 5(a) to (e) illustrate the function of the reticle tester of the present invention, wherein:

FIG. 5(a) illustrates a scanned part of FIG. 3, enlarged to make it correspond to the following waveforms;

FIG. 5(b) is the waveform of the output from a first wave shaping circuit 8 (at connecting line 101) in FIG. 4;

FIG. 5(c) is the waveform of the output from a second wave shaping circuit 10 (at connecting line 102) in FIG. 4;

FIG. 5(d) is the waveform of the output from the control unit 55 (at connecting line 103) in FIG. 4; and FIG. 5(e) is the waveform of the output from the comparator 111 (at connecting line 104) in FIG. 4.

DESCRIPTION OF PREFERRED EMBODIMENT

Before discussing the present invention, a known database inspection method using a prior art reticle tester will be explained.

Figure 1:
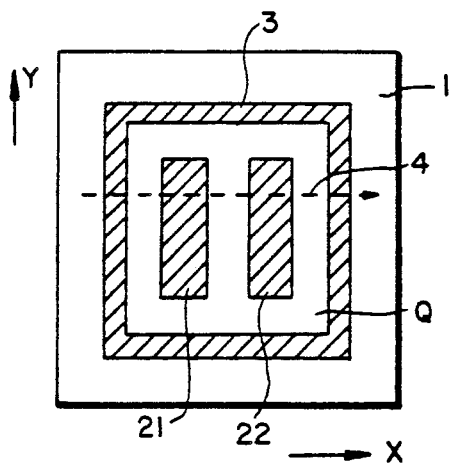
FIG. 1 is a schematic plan view of the reticle pattern to be inspected.

FIG. 1 shows illustratively a plan view of the reticle pattern to be inspected. In practical reticles, the pattern is more complicated than the one shown in FIG. 1, in which only a small number of rectangular patterns are shown for the sake of explanation. In the figure, reference numeral 1 is a reticle, and reference numerals 21, 22, and 3 are the patterns on the reticle 1. The patterns are printed on an optically transparent material with an opaque film, and are shown as simple patterns for the sake of explanation, namely, the patterns 21 and 22 are arranged in parallel with the same shape and size and are surrounded by the pattern 3. Reference numeral 4 shows an optical scanning line for the database inspection of the reticle 1, which scans optically the surface of the reticle from left to right in the figure along the X axis.

Figure 2:
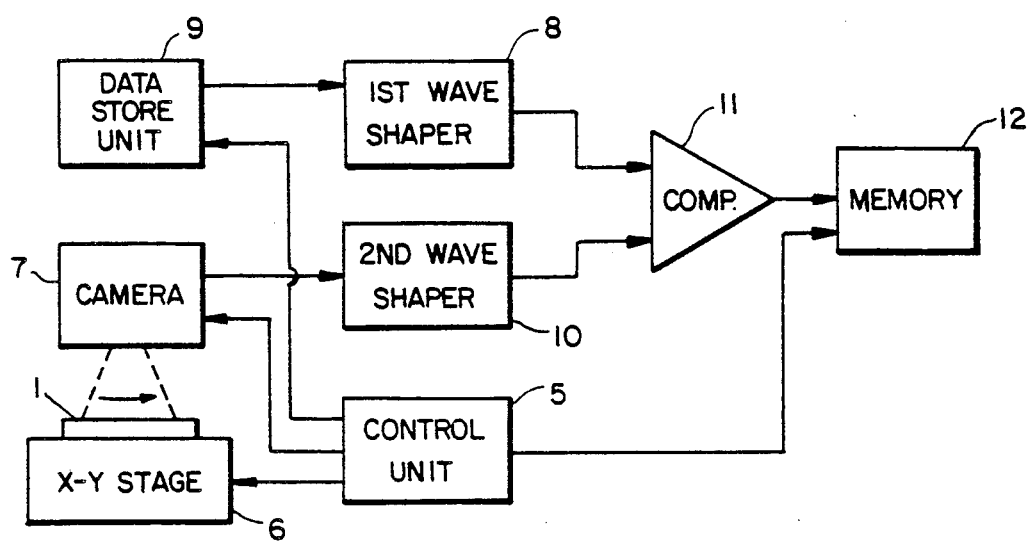
FIG. 2 shows a block diagram of the prior art reticle tester.

FIG. 2 shows a block diagram of the prior art reticle tester. In the figure, each unit or circuit operates as follows.

reference numeral 1 shows a reticle as in FIG. 1 which is placed on an X-Y stage 6 described below;

reference numeral 5 shows a control unit which outputs several control signals for the operation of the reticle tester;

reference numeral 6 shows the X-Y stage on which the reticle 1 is placed to be inspected and which is scanned in a Y axis direction by a precision mechanism, and from the top to the bottom, as indicated in FIG. 1, responsive to a control signal from the control unit 5;

reference numeral 7 shows a camera with which the reticle 1 is scanned in an X axis direction in synchronization with the control signal from the control unit 5, and the camera 7 outputs electronic video signals corresponding to the scanning of camera 7 and the X-Y stage 6;

reference numeral 9 shows a data store unit which stores the inspection data in the storage medium, such as on magnetic tapes, and outputs the data video signals in cooperation with the scans of camera 7 and X-Y stage 6 under the control of the control signal from the control unit 5;

reference numeral 8 shows a first wave shaping circuit which shapes the output from the data store unit 9 to provide "data video signals" for the comparator 11 having a designated amplitude;

reference numeral 10 shows a second wave shaping circuit which shapes the output from the camera 7 to provide "optical video signals" for the comparator 11 having the same amplitude as the designated amplitude of the data video signals from the wave shaping circuit 8, except when there is a defect in the scanned pattern;

reference numeral 11 shows a comparator which compares the data video signals and the optical video signals. Both signals go into the comparator 11 with the same timing as controlled by the control unit 5, and the comparison is also made by a control signal from the control unit 5. When the amplitude of the data video signals and the optical video signals are equal, that is, when the pattern has no defect, the comparator 11 will provide no output, but if the pattern has a defect, the comparator 11 outputs a fault signal; and reference numeral 12 shows a memory which memorizes the fault signals in the address of the memory corresponding to the pattern of the photomask reticle according to the control signal from the control unit 5.

The fault signals in memory 12 can be provided visually on a video display or on a printed paper, so that the result of the inspection can be checked. From the result, a defect can be corrected if such is possible, and the fault data can be accumulated for the quality control of the semiconductor device fabrication.

FIG. 1 shows a simple reticle pattern as an example, so that there is no problem with the data volume, even in connection with the prior art reticle tester. However, as mentioned before, recent reticle patterns are becoming so complicated that a very large space for stocking the media for the data has come to be required. Therefore, it has become almost impossible to apply the database inspection using the prior art reticle tester to the larger scale integrated circuits.

However, a semiconductor device having high packing density is generally composed of a plurality of elements each having the same respective patterns, so that the reticle also has a plurality of patterns of the same respective shapes and sizes. The present invention is applicable in this context. That is, the patterns having the same respective shape and size are not necessary to be inspected by the database method individually, since it is sufficient to inspect only one pattern by the database inspection method. If the patterns each having the same shape and size can be left out of the database inspection, the space required for the storage media could be greatly reduced. having the same respective shape and size, wherein the reticle tester inspects the picked u pattern by the database inspection method, and then the other remaining patterns of the same size and shape are inspected by the usual pattern comparing inspection method, setting the picked up pattern as the standard pattern for the comparisons.

As explained above, by applying both methods of the database inspection and the pattern comparing inspection, the problem of the prior art can be solved, because the data of all the patterns each having the same shape and size is not necessary to be stored, and still the inspection accuracy can be kept high. This is an advantage of the present invention, that is, the present invention requires only one pattern of the inspecting data for the patterns each having the same respective shape and size for the database inspection, and the other remaining patterns having the same shape and size are inspected quickly by the pattern comparing inspection.

Figure 3:
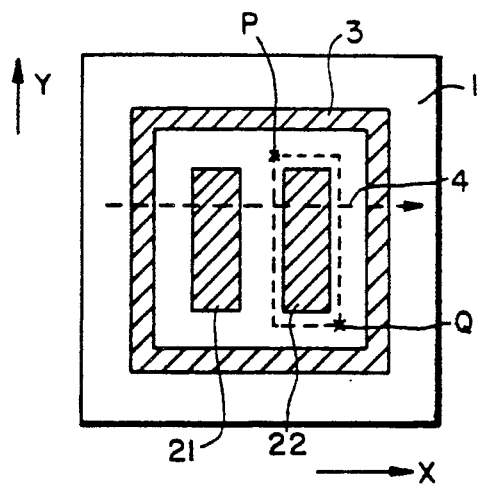
FIG. 3 shows a schematic plan view of a reticle having the same pattern of FIG. 1, and illustrating the exclusion region of the present invention.

FIG. 3 shows a plan view of a reticle having the same shape and size as that of FIG. 1, for illustrating the present invention. In the figure, the reference numerals and symbols are the same as in FIG. 1, except for P and Q. The symbols P and Q are the points of the X-Y coordinates which designate what is referred to herein as an "exclusion region" P-Q, namely, a dotted square including the pattern 22 which is the same as the pattern 21.

When pattern 21 has been inspected previously by the database inspection, and the pattern comparing inspection method is applied to the region P-Q for comparing pattern 22 to pattern 21, the patterns within the region P-Q can be excluded from the object of the database inspection. By doing this, the data for the database inspection, that is, the space for stocking the magnetic tapes, can be reduced, and the time for the inspection can be greatly reduced.

Figure 4:
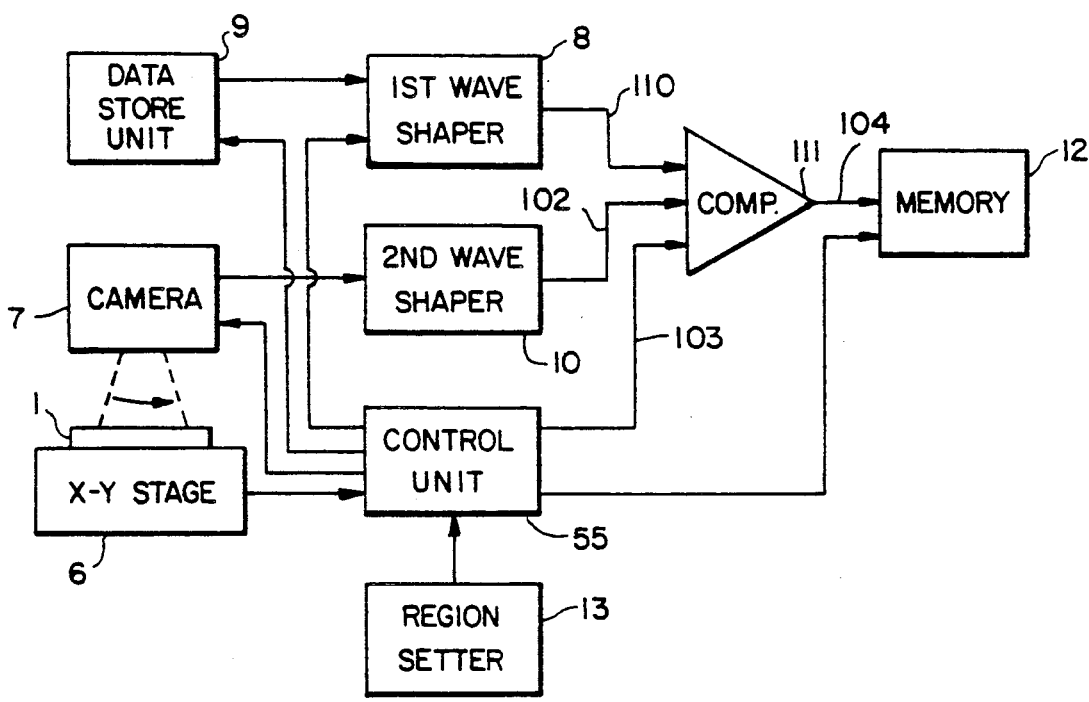
FIG. 4 shows a block diagram of a reticle tester for the present invention.
Figure 5:
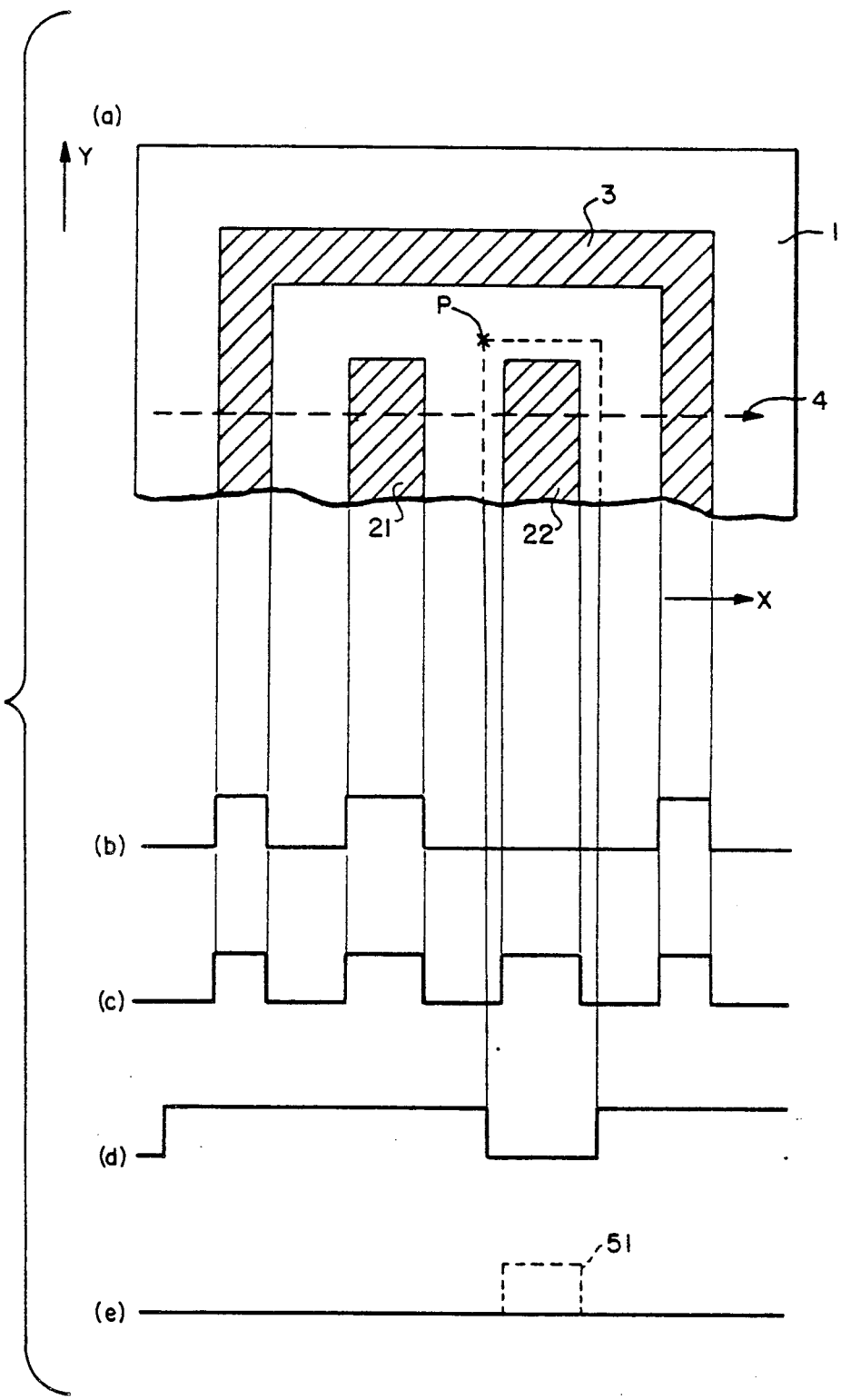

FIG. 4 shows a block diagram of an apparatus of the present invention, namely an improved reticle tester, and FIGS. 5 (a) to 5(e) illustrate the function of the reticle tester of the present invention for excluding the patterns having the sam shape and size from the database inspection.

In FIG. 4, each block with the same reference numeral as in FIG. 2 has the same function. Reference numeral 13 is a "region setter" which sets the exclusion regions such as the exclusion region P-Q in FIG. 3, to prevent the database inspection of the patterns within the exclusion regions such as pattern 22 in FIG. 3. The control unit 55 and the comparator 111 have functions similar to the those of the control unit 5 and the comparator 11 in FIG. 2 respectively, but are modified to set the exclusion regions.

FIG. 5(a) shows the scanning of a part of FIG. 3 that is enlarged in correspondence with the following waveforms. FIGS. 5(b), (c), (d), and (e) show the waveforms on the lines of FIG. 4 indicated by the reference numerals 110, 102, 103, and 104, respectively, when the optical scanning is made on the reticle 1 as shown in FIG. 5(a).

At the beginning of the reticle inspection, each group of patterns having the same respective shape and size are selected from the design data for the reticle pattern, such as a group including patterns 21 and 22 in FIG. 3, as an example, and a pattern is picked up from each group, such as pattern 21 in FIG. 3. The address information of the exclusion region, for example P-Q in FIG. 3, from the design data, are set into the control unit 55 by an inspector to exclude the exclusion regions from the database inspection. The picked up pattern is inspected by the database inspection method, and is also used as the standard pattern for the pattern comparing inspection.

In FIG. 4, when the addresses of P and Q are given to region setter 13 by the inspector, the region setter 13 controls the control unit 55 to designate the exclusion regions, such as the exclusion region P-Q in FIG. 3 or FIG. 5(a) (wherein only P is indicated). When camera 7 scans the reticle 1 such as on the optical scanning line 4 in FIG. 3 or FIG. 5(a), the control unit 55 controls a first wave shaping circuit 8 so that the data video signal at line 110 goes to the comparator 111 with the pattern 22 being removed in the exclusion region P-Q as shown in FIG. 5(b). Meanwhile, the camera video signal goes into the comparator 111 with the waveform on the line 102, as shown in FIG. 5(c). The comparator 111 compares a coincidence waveform according to agreement of the waveforms of FIGS. 5(b) and 5(c), as long as the gate signal applied to the line 103 from the control unit 55 is ON, as shown in FIG. 5(d), so that the output signal from the comparator 111 at line 104 has no fault information as shown in FIG. 5(e). If the gate signal on line 103 is ON while scanning the pattern 22 in the exclusion region, the comparator 111 would provide a fault signal as shown by the dotted waveform 51 in FIG. 5(e). The fault signals from the comparator 111 go into the memory 12 if there are some defects on the reticle pattern, and are memorized in each address under the control of the control unit 55. The result of the inspection can be subsequently checked by the signals read out from the memory 12 as indicated above.

After the pattern 21 is judged to be correct by the above data base inspection, the patterns in the exclusion regions such as the pattern 22 can be inspected by the usual prior art method, namely the pattern comparing inspection method, using the pattern 21 as the standard pattern for the comparison.

The effect of the present invention for the fabrication of the semiconductor die in actual manufacture is as follows, in comparison with the prior art inspection method:

the volume of the store media for the data in the present invention is reduced to as little as one fourth of that in the prior art;

the time spent for designing the inspection data in the present invention is about 80 minutes, which is less than half of that in the prior art wherein about 3 hours was needed; and the time spent for the inspection of the semiconductor device in the present invention is about 10 minutes, which is as little as one fourth of that in the prior art wherein about 4 minutes was needed.

Therefore the effect of the present invention can be said to be as much as a factor of four, in terms of the savings in space and time, in comparison with the prior art inspection method.

What is claimed is:

1. A machine method of inspecting a photomask having a pattern area, a first pattern in the pattern area, a plurality of second patterns in the pattern area, each of said second patterns having the same shape and size and being different from said first pattern, said method comprising the steps of:
    (a) storing in a memory a database defining the first pattern and one of the second patterns;
    (b) generating data video signals in response to reading the database out of the memory;
    (c) providing camera video signals in response to optically scanning the pattern area and in synchronism with generation of the data video
    (d) providing an exclusion address defining an exclusion area of the photomask that includes another one of the second patterns;
    (e) comparing the data video signals and the camera video signals using the exclusion address;
    (f) determining whether or not the one of the second patterns includes a fault based on the comparing of step (e);
    (g) visually comparing the another one of the second patterns with the one of the second patterns when the one of the second patterns does not include a fault.

2. The method of claim 1, said database being a design database used in the fabrication of said photomask reticle.

3. The method of claim 1, said database being an inspection database.

4. The method of claim 1, wherein step c) includes the substep of:
    providing the camera video signals using a reticle tester that includes a region setter and step d) includes the substep of:
    storing the location of the exclusion area using the address signal provided by the reticle tester.

5. An apparatus for inspecting a photomask having a pattern area, a first pattern in the pattern area, and a plurality of second patterns in the pattern area, each of said second patterns having the same shape and size and being different from said first pattern, said apparatus comprising:
    means for optically and electrically detecting said first pattern and said plurality of second patterns, and for providing a detected pattern signal comprising a first pattern signal obtained by detecting the first pattern and second pattern signals obtained by detecting the plurality of second patterns;
    means for receiving an exclusion address identifying one of the second patterns;
    means for storing a database including standard pattern information corresponding to a standard pattern for the first pattern and a standard pattern for the second patterns;
    means for providing a standard data signal corresponding to the standard pattern for the first pattern and the standard pattern for the second patterns in synchronism with the detected pattern signal; and means for comparing the standard data signal corresponding to the standard pattern for the first pattern with the first pattern signal, and for comparing the standard pattern for the second patterns with the second pattern signals in accordance with the exclusion address; and means for visually comparing the remaining ones of the second patterns with the one of the second patterns.

6. An apparatus for inspecting the patterns of a component associated with the fabrication of semiconductor devices, wherein the patterns include at least one set of the patterns each having an identical size and shape, and at least one other pattern, said apparatus comprising:

means for optically and electrically detecting said patterns of said component and for producing first detected pattern signals comprising a first pattern signal corresponding to the other pattern and second pattern signals corresponding to the at least one set of the patterns;

means for storing a pattern database including (a) first data defining a standard for the other pattern and second data defining a standard for one pattern of the at least one set of the patterns;

means for producing data signals corresponding to the stored pattern database;

means for receiving an exclusion address identifying a first portion of the second patterns; and means for comparing the first portion of the second patterns with the data signals in accordance with the exclusion address; and means for visually comparing the remaining portion of the second patterns with the first portion of the second patterns.

7. A reticle testing apparatus for inspecting the patterns of a reticle associated with the fabrication of semiconductor devices, wherein the patterns include at least one set of the patterns each having an identical size and shape, and at least one other pattern, said apparatus comprising:

means for optically and electrically detecting the patterns of the reticle, for producing first detected pattern signals comprising a first pattern signal corresponding to the other pattern and second pattern signals corresponding to the at least one set of the patterns;

means for storing a pattern database defining one pattern of the one set of patterns and defining the other pattern;

means for producing data signals corresponding to the stored pattern database;

region setting means for setting a storing location information defining an exclusion region;

means for selecting a first portion of the second pattern signals that corresponds to the one pattern of the one set of patterns using said location information;

means for electrically comparing said first portion of said second pattern signals with said data signals; and means for visually comparing the other patterns of the one set of patterns using the one pattern of the one set of patterns as a standard for the comparison.

* * * * *

UNITED STATES PATENT AND TRADEMARK OFFICE
CERTIFICATE OF CORRECTION

PATENT NO. : 5,125,040

DATED : June 23, 1992

INVENTOR(S) : SHOGO MATSUI and KENICHI KOBAYASHI

It is certified that error appears in the above-identified patent and that said Letters Patent is hereby corrected as shown below:

Column 4, line 18, after "reduced." insert --This can be achieved by picking up one pattern from the patterns--;

line 19, "u" should be --up--;

line 59, "sam" should be --same--.

Column 6, line 20, after "video" insert --signals;--;

line 28, after "(e);" insert --and--.

Signed and Sealed this

Seventh Day of September, 1993

Attest:

BRUCE LEHMAN

Attesting Officer      Commissioner of Patents and Trademarks